United States Patent
Tsukiji

(10) Patent No.: US 10,064,786 B2
(45) Date of Patent: Sep. 4, 2018

(54) CONTAINER-HOLDING TRAY

(71) Applicant: DAIKYO SEIKO, LTD., Tochigi (JP)

(72) Inventor: Daisuke Tsukiji, Tochigi (JP)

(73) Assignee: DAIKYO SEIKO, LTD., Tochigi (JP)

(*) Notice: Subject to any disclaimer, the term of this patent is extended or adjusted under 35 U.S.C. 154(b) by 174 days.

(21) Appl. No.: 14/434,032

(22) PCT Filed: Oct. 17, 2013

(86) PCT No.: PCT/JP2013/078180
§ 371 (c)(1),
(2) Date: Apr. 7, 2015

(87) PCT Pub. No.: WO2014/069244
PCT Pub. Date: May 8, 2014

(65) Prior Publication Data
US 2015/0272827 A1    Oct. 1, 2015

(30) Foreign Application Priority Data
Oct. 31, 2012 (JP) .................................. 2012-240350

(51) Int. Cl.
*A61M 5/00* (2006.01)
*A61J 1/16* (2006.01)
*B65D 1/36* (2006.01)

(52) U.S. Cl.
CPC ............... *A61J 1/16* (2013.01); *A61M 5/002* (2013.01); *A61M 5/008* (2013.01); *B65D 1/36* (2013.01); *F04C 2270/0421* (2013.01)

(58) Field of Classification Search
USPC ............... 206/564, 203, 363, 438, 439, 370; 220/518
See application file for complete search history.

(56) References Cited

U.S. PATENT DOCUMENTS
3,398,828 A * 8/1968 Allen ................... B65D 25/107
206/564
4,928,841 A * 5/1990 Arthurs .................. B65D 71/70
206/203
(Continued)

FOREIGN PATENT DOCUMENTS
FR    2771390    5/1999
JP    60-002610    1/1985
(Continued)

OTHER PUBLICATIONS
xtended European Search Report, issued in the corresponding European patent application No. 3851389.0/1662, dated May 3, 2016, 7 pages.
(Continued)

*Primary Examiner* — Jacob K Ackun
(74) *Attorney, Agent, or Firm* — Hamre, Schumann, Mueller & Larson, P.C.

(57) ABSTRACT

The present invention relates to a container-holding tray 1 for holding a plurality of bottomed cylindrical medical containers 50 side by side. The container-holding tray 1 includes the bottom surface part 2 and the container holding convex parts 4 formed on the bottom surface part 2 and configured to hold the medical containers 50, wherein each of the container holding convex parts 4 has a tapered shape that is thin on the upper end side thereof, the plurality of the container holding convex parts 4 are configured to a lattice arrangement on the bottom surface part 2, and simultaneously four of the container holding convex parts 4 are integrated, thereby a container housing part 6 corresponding to one of the medical containers is formed, and the medical containers 50 are configured to be brought into contact with any point from the upper end to the lower end of the four convex parts 4 so as to be held.

5 Claims, 6 Drawing Sheets

(56) References Cited

U.S. PATENT DOCUMENTS

| | | | | |
|---|---|---|---|---|
| 5,105,948 | A * | 4/1992 | Morris | B65D 71/70 206/427 |
| 5,248,035 | A * | 9/1993 | Gallagher | B65D 1/24 206/427 |
| 5,600,896 | A * | 2/1997 | Lin | F26B 9/003 34/107 |
| 5,868,244 | A * | 2/1999 | Ivanov | B65B 11/50 206/439 |
| 5,968,451 | A * | 10/1999 | Iwamoto | B65B 55/025 422/303 |
| 6,193,064 | B1 * | 2/2001 | Finneran | B01L 3/5085 134/166 R |
| 6,216,885 | B1 | 4/2001 | Guillaume | |
| 6,572,819 | B1 * | 6/2003 | Wu | A61L 2/26 206/438 |
| 7,296,678 | B2 * | 11/2007 | Raynal-Olive | A61L 2/208 206/370 |
| 7,428,807 | B2 * | 9/2008 | Vander Bush | A61M 5/002 206/432 |
| 7,892,504 | B2 * | 2/2011 | Taike | B01L 3/50855 206/565 |
| 8,100,263 | B2 * | 1/2012 | Vanderbush | A61M 5/002 206/366 |
| 8,136,679 | B2 * | 3/2012 | Fry | B01L 3/50855 211/85.18 |
| D673,296 | S * | 12/2012 | Fry | A61M 5/002 D24/227 |
| 8,360,238 | B2 * | 1/2013 | Nicoletti | B65D 5/503 206/443 |
| 8,469,185 | B2 * | 6/2013 | Nicoletti | B65D 77/0446 206/203 |
| 8,906,318 | B1 * | 12/2014 | Cheung | A61L 2/07 422/292 |
| 9,427,710 | B2 * | 8/2016 | Jansen | B01D 69/12 |
| 9,555,911 | B2 * | 1/2017 | Pawlowski | B01L 9/06 |
| 9,610,126 | B2 * | 4/2017 | Griffin | A61B 50/30 |
| 2005/0269239 | A1 * | 12/2005 | Apps | B65D 1/243 206/557 |
| 2006/0016156 | A1 | 1/2006 | Bush et al. | |
| 2007/0157564 | A1 | 7/2007 | Vander Bush et al. | |
| 2008/0314771 | A1 | 12/2008 | Barbalho et al. | |
| 2009/0065458 | A1 * | 3/2009 | Murray | B01L 9/06 211/85.18 |
| 2009/0100802 | A1 | 4/2009 | Bush et al. | |
| 2009/0288977 | A1 | 11/2009 | Vanderbush et al. | |
| 2010/0294734 | A1 * | 11/2010 | Taike | B01L 3/50855 211/85.13 |
| 2012/0181285 | A1 | 7/2012 | Krauss et al. | |
| 2015/0122693 | A1 * | 5/2015 | Deutschle | B65D 25/108 206/562 |
| 2015/0166217 | A1 * | 6/2015 | Deutschle | B65D 25/108 53/425 |

FOREIGN PATENT DOCUMENTS

| | | |
|---|---|---|
| JP | 2001-178799 | 7/2001 |
| JP | 2001-327577 | 11/2001 |
| JP | 2008-505029 | 2/2008 |
| NO | 2009015862 | 2/2009 |
| NO | 2011015896 | 10/2011 |
| TK | 2013043073 | 3/2013 |
| WO | 2011135085 | 11/2011 |

OTHER PUBLICATIONS

International Search Report, dated Jan. 21, 2014; PCT/JP2013/078180 (2 pages).

Japanese Office Action, issued in the corresponding Japanese patent application No. 2014-544424, dated Dec. 1, 2015, 3 pages.

* cited by examiner

[Fig. 1]
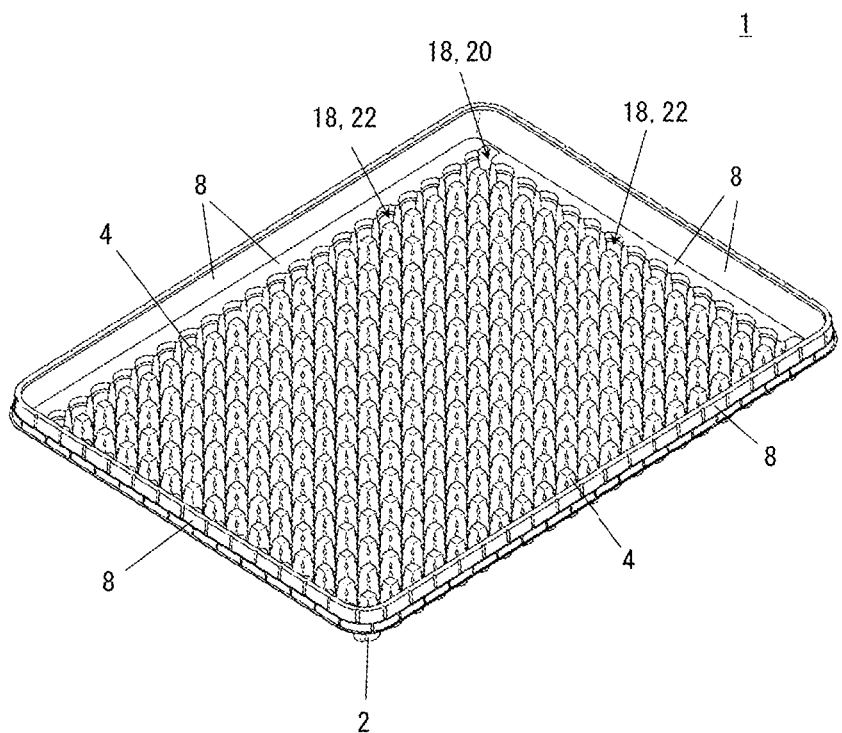
[Fig. 2]
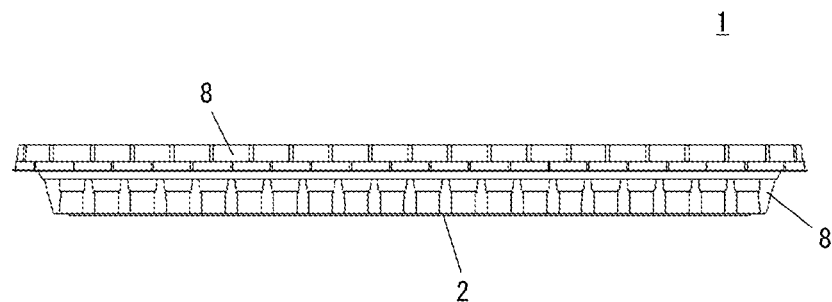

[Fig. 3]
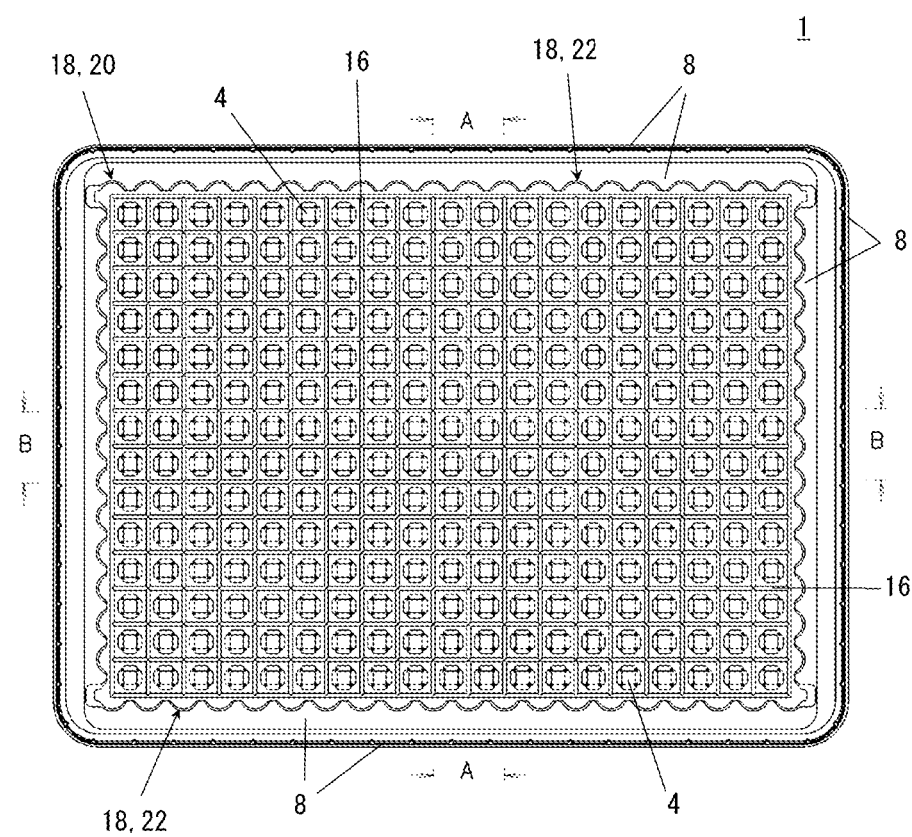

[Fig. 4]
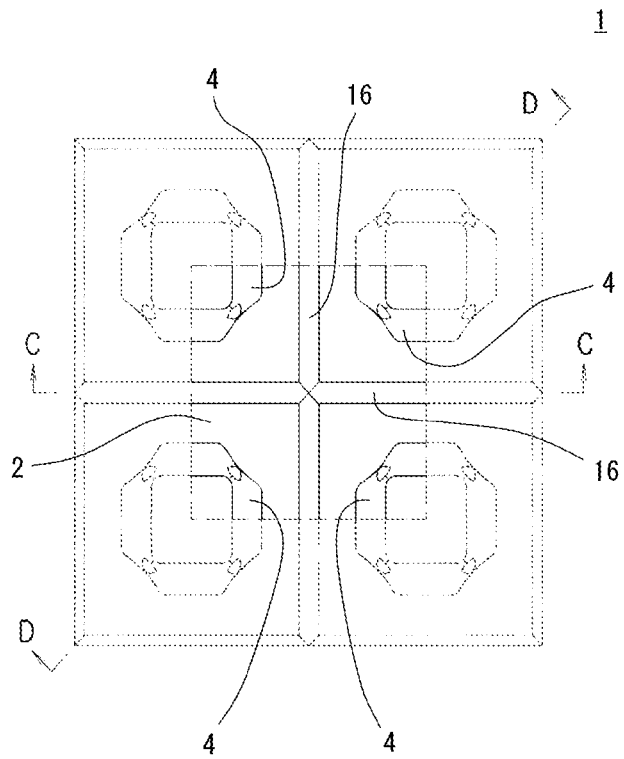
[Fig. 5]
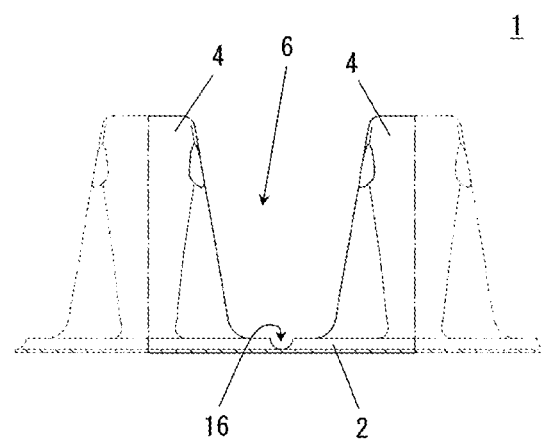

[Fig. 6]
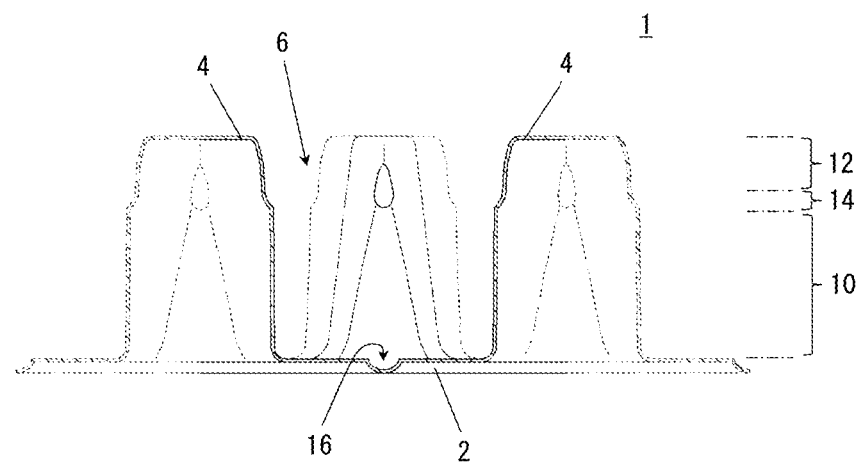
[Fig. 7]
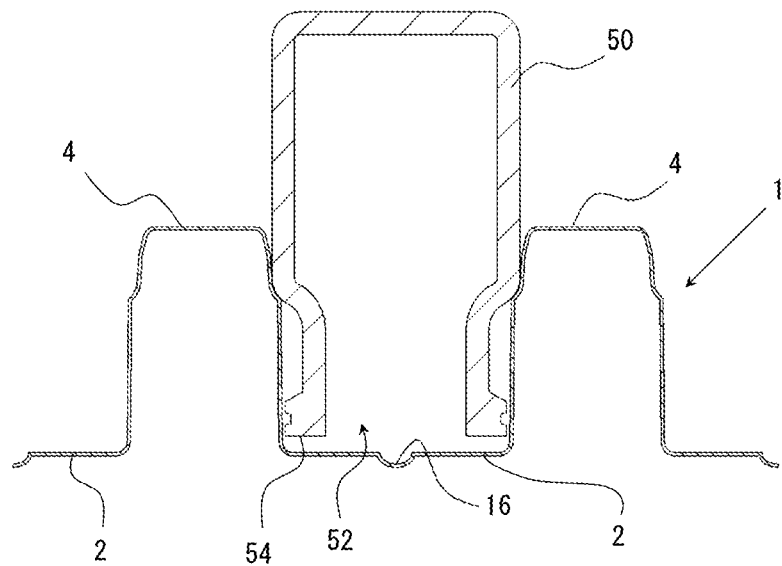

[Fig. 8]
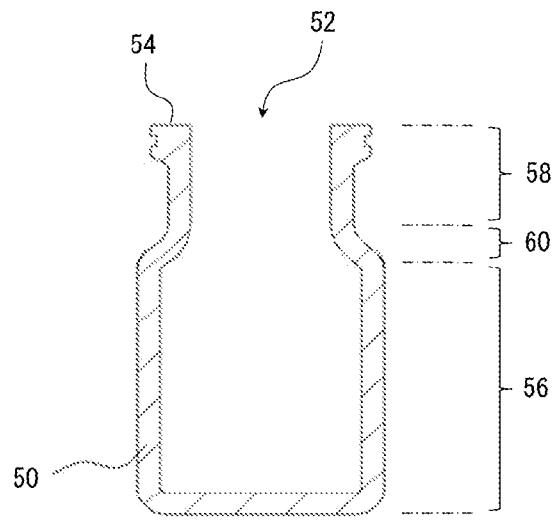
[Fig. 9]
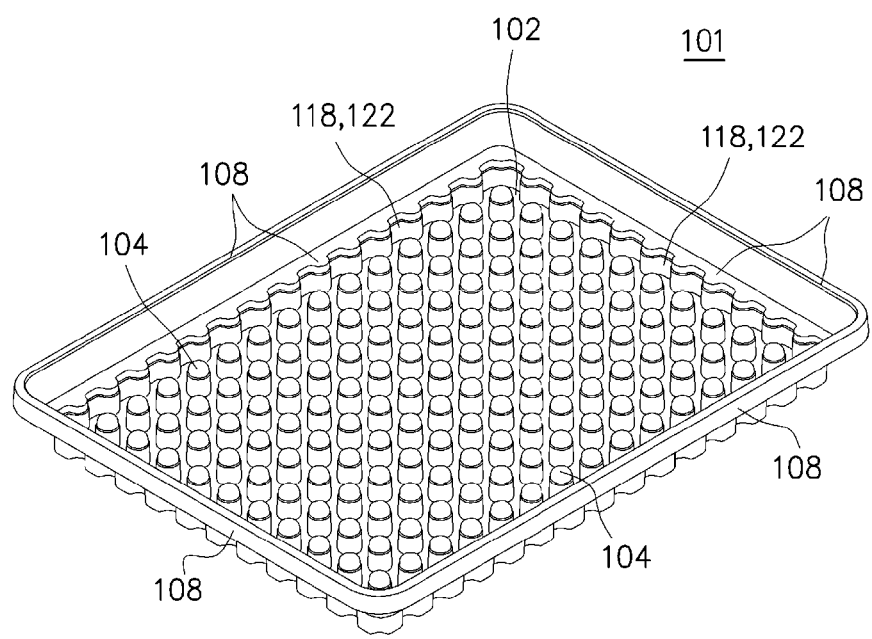

[Fig. 10]
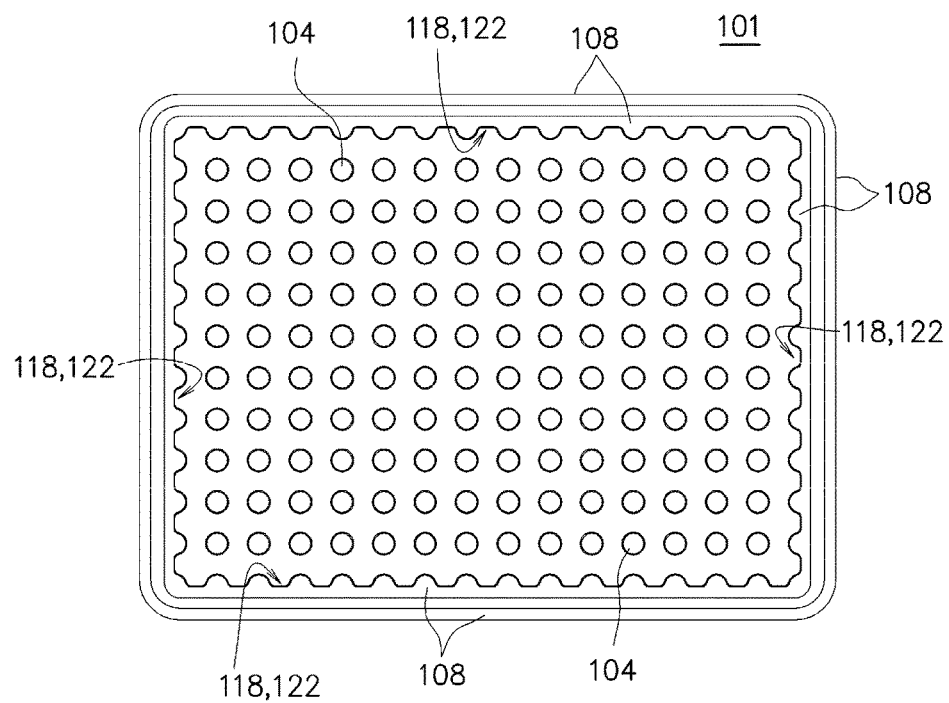
[Fig. 11]
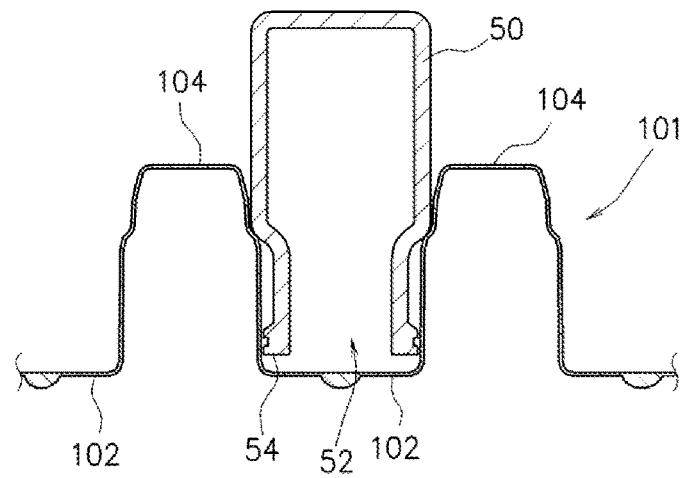

CONTAINER-HOLDING TRAY

TECHNICAL FIELD

The present invention relates to a container-holding tray for holding a plurality of bottomed cylindrical medical containers such as vial, syringe barrel side by side.

BACKGROUND ART

A medical container such as vial, syringe barrel is a container into which a liquid medicine, a specimen collected from the human body or the like is injected, thus if a microorganism is adhered to the surface of the container or the like, it may have a serious impact on the liquid medicine and the specimen. Accordingly, the medical container is usually used after sterilization is carried out.

As a method of the sterilization, a high-pressure steam sterilization is widely adopted, the method being configured such that the medical container of a sterilization object is sterilized by being exposed to a high temperature and high pressure steam atmosphere for a predetermined time (121° C., 20 minutes or the like). In addition, in the high pressure steam sterilization, for the purpose of sterilizing or carrying a great number of medical containers at the same time, a container-holding tray capable of holding a plurality of medical containers in an alignment state is utilized.

For example, a tray for medical container is disclosed, the tray being configured such that a plurality of depressions along the head part or the bottom part of the medical container are formed in the floor of the tray (refer to Patent Literature 1). In Patent Literature 1, there is also a description stating that vacuum grooves may be formed in the floor of the tray, the vacuum grooves crossing the floor so as to be brought into contact with each of the plurality of the depressions.

CITATION LIST

Patent Literature

Patent Literature 1: Japanese Translation of PCT international Application Publication No. JP2008-505029A

SUMMARY OF INVENTION

Technical Problem

The above-mentioned tray mounts the medical containers (hereinafter, may be merely referred to as "container") thereon in accordance with the depressions of the floor, thereby there is an advantage that the plurality of the containers can be aligned in an appropriate position and direction (faced upward, faced downward) simply and quickly. However, it has a problem to be solved as shown below.

First, if the above-mentioned tray is used and the high-pressure steam sterilization is carried out in the condition that and the containers are mounted on the tray while facing upward, there is a risk that the steam condenses in the vicinity of the opening part of the containers into droplets of water, and the droplets of water flow into the inside of the containers. If the droplets of water flow into the inside of the containers, it takes a long time to dry the containers so as to consume excessive energy, thus it is not preferable in terms of both cost and work efficiency.

On the other hand, if the high-pressure steam sterilization is carried out in the condition that the containers are mounted on the above-mentioned tray while facing downward, the opening part of the containers is closed by the floor of the tray, thus it is difficult for the high-pressure steam to flow into the inside of the containers even if the vacuum grooves are formed. Consequently, there is a risk that sterilization cannot be carried out sufficiently up to the inside of the containers. In addition, the droplets of water due to the condensation of the steam store in the floor of the tray, and the water adheres to the vicinity of the opening of the containers, thus there is also a risk that the water flows into the inside of the containers.

Furthermore, the depressions are merely a positioning means for the containers, thus only by means of the depressions, it is impossible for the containers to be stably held so as not to fall down. Accordingly, in the tray, a method is adopted, the method being configured such that a plurality of the containers are densely filled in the tray so that the containers are held in such a manner that the containers are mutually supported. However, the method cannot stably hold the containers unless the containers are densely filled in the tray, thus an effect thereof on stably holding each of the containers is low. Consequently, Patent Literature 1 also discloses a method configured such that a nest-like plate is separately disposed in the tray, and the containers are inserted into the sleeves of the nest-like plate one by one so as to be held thereby. According to the method, each of the containers can be stably held, but it needs a separate member such as the nest-like plate, thus the tray structure becomes complicated, in addition, the operation for holding the containers becomes troublesome.

The present invention has been provided for solving the problem of the conventional technology. Namely, the present invention is configured to provide a container-holding tray that is capable of preventing water from flowing to the inside of the container and simultaneously surely sterilizing the inside of the container during high pressure steam sterilization, and that makes it possible to stably hold the container by a simple method.

Solution to Problem

The present inventors have diligently studied with regard to the above-mentioned problem. As a result, the inventors et al. have found out that a great number of the container holding convex parts having a tapered shape are formed in the bottom surface part of the tray, and the medical containers are surrounded by the three or four of the container holding convex parts neighboring to each other so as to be held, thereby the above-mentioned problem can be solved, so that the present invention has been completed. Namely, according to the present invention, the following container-holding tray is provided.

The container-holding tray according to the present invention is a container-holding tray for holding a plurality of bottomed cylindrical medical containers side by side. In addition, the container-holding tray according to the present invention includes a bottom surface part and container holding convex parts formed on the bottom surface part and configured to hold the medical containers, wherein each of the container holding convex parts has a tapered shape that is thick on the lower end side and is thin on the upper end side, the plurality of the container holding convex parts are configured to be a lattice arrangement or a zigzag arrangement on the bottom surface part, and simultaneously three or four of the container holding convex parts neighboring to each other are integrated so as to surround an inner space thereof, thereby a container housing part corresponding to one of the medical containers is formed, and the medical container is configured to be brought into contact with any point from the upper end to the lower end of the three or four of the container holding convex parts constituting the container housing part so as to be held.

It is preferable that the container-holding tray according to the present invention is configured such that the plurality of bottomed cylindrical medical containers are held side by side in a state that an opening thereof is faced downward, and the end of the opening of the medical containers is configured to be kept in a state of non-contact with the bottom surface part.

It is preferable that the container-holding tray according to the present invention is configured such that the plurality of bottomed cylindrical medical containers are held side by side in a state that the opening thereof is faced downward, and the medical containers include a barrel part having a large diameter, located on the bottom side, a neck part having a small diameter located on the opening part side, and a shoulder part connecting the barrel part and the neck part, and having a diameter narrowed from the barrel part toward the neck part.

In addition, it is preferable that the container-holding tray according to the present invention is configured such that the container housing part is configured such that the upper end side thereof is formed larger than the barrel part of the medical container and simultaneously the lower end side thereof is formed smaller than the barrel part of the medical container, and the barrel part of the medical container is configured to be brought into contact with any point from the upper end to the lower end of the three or four of the container holding convex parts so as to be held, and the length from the point to the lower end of the container housing part is formed so as to be longer than the total length of the shoulder part and the neck part of the medical container.

Furthermore, it is preferable that the container-holding tray according to the present invention is configured such that the each of the container holding convex parts includes a large diameter part located on the lower end side, a small diameter part located on the upper end side, and a step part connecting the large diameter part and the small diameter part, and having a diameter narrowed from the large diameter part toward the small diameter part, the barrel part of the medical container is configured to be brought into contact with the step part so as to be held, and the length from the step part to the lower end of the container housing part is formed so as to be longer than the total length of the shoulder part and the neck part of the medical container.

Still furthermore, it is preferable that the container-holding tray according to the present invention is configured such that a plurality of ventilation grooves are formed so as to pass through between the container holding convex parts.

Advantageous Effects Of Invention

The container-holding tray according to the present invention is capable of preventing water from flowing to the inside of the container and simultaneously surely sterilizing the inside of the container during high pressure steam sterilization. In addition, the container-holding tray makes it possible to stably hold the container by a simple method.

BRIEF EXPLANATION OF THE DRAWINGS

FIG. 1 is a perspective view schematically showing an embodiment of a container-holding tray according to the present invention;

FIG. 2 is a side view schematically showing a state of the container-holding tray shown in FIG. 1, when seen from the side thereof;

FIG. 3 is a plan view schematically showing a state of the container-holding tray shown in FIG. 1, when seen from the upper part thereof;

FIG. 4 is an enlarged plan view schematically enlarging and showing a part of the container-holding tray shown in FIG. 3, the part being indicated by references A and B;

FIG. 5 is an enlarged sectional view schematically enlarging and showing a state of the container-holding tray shown in FIG. 4, when being cut along the line C-C;

FIG. 6 is an enlarged sectional view schematically enlarging and showing a state of the container-holding tray shown in FIG. 4, when being cut along the line D-D;

FIG. 7 is an enlarged end view schematically enlarging and showing a D-D cut end face of the container-holding tray shown in FIG. 4 in the use condition thereof;

FIG. 8 is an end view schematically showing a specific structure of the medical containers shown in FIG. 7;

FIG. 9 is a perspective view schematically showing another embodiment of the container-holding tray according to the present invention;

FIG. 10 is a plan view schematically showing a state of the container-holding tray shown in FIG. 9, when seen from the upper part thereof; and FIG. 11 is a plan view schematically enlarging and showing the vicinity of the container holding convex part in the use condition of the container-holding tray shown in FIG. 9.

DESCRIPTION OF EMBODIMENTS

Hereinafter, the present invention will be described in more detail giving preferable embodiments. The present invention is, however, not limited to the following Examples, but includes all the modifications and alternative constructions having the matters used to specify the invention.

[1] Medical Container:

The container-holding tray according to the present invention is configured such that the holding target thereof is a bottomed cylindrical medical container. The "medical container" includes an instrument (syringe barrel and the like) into which a liquid medicine or a specimen may be injected, other than the so-called container (vial and the like).

The "cylindrical shape" means a shape that has an inner space formed therein, the inner space directing from one end part to another end part. For example, a circular cylindrical shape; an angular cylindrical shape such as a rectangular cylindrical shape; and other shapes (approximately circular cylindrical and the like) equivalent to these shapes are included.

The "cylindrical shape" includes, however, not only a shape having a constant outer diameter and a constant inner diameter from one end part to another end part such as a circular cylindrical shape, an angular cylindrical shape, but also a different diameter cylindrical shape having different parts in the outer diameter and the inner diameter.

For example, as a form of a vial, a medical container 50 shown in FIG. 8 is included, the medical container 50 having a shape that is constituted of a barrel part 56 of a large diameter positioned on the bottom side, a neck part 58 of a small diameter positioned on the side of the opening part 52, and a shoulder part 60 connecting the barrel part 56 and the neck part 58 and having a diameter narrowed from the barrel part 56 toward the neck part 58. The above-mentioned shape is also included in the "cylindrical shape". Further, as the vial, there is one having a form that a lip forming the opening part is directly combined with the shoulder part, and the neck part is substantially absent or the neck part is extremely short. Naturally, the above-mentioned shape is also included in the "cylindrical shape".

The "bottomed" shape means a shape that has a bottom part configured to close one end part of the cylindrical structure like the vial. The "bottom part" described here is, however, not needed to have a shape that is perfectly closed, and not needed to be positioned on the lower side of the container when it is used. For example, a syringe barrel is configured such that one end part (tip part) of the cylindrical structure is closed, and it has the "bottom part" on the tip part side, and a through hole is formed in the "bottom part", thus a state that is perfectly closed is not attained. The above-mentioned shape is also included in the "bottomed" shape.

[2] Container-Holding Tray:

The container-holding tray according to the present invention is a tray configured to hold a plurality of bottomed cylindrical medical containers side by side. If the above-mentioned tray is used, a plurality of medical containers can be subjected to high pressure steam sterilization at the same time, and can be carried as they are.

In addition, the container-holding tray according to the present invention is configured to hold a plurality of bottomed cylindrical medical containers in a state that the opening thereof is faced upward or downward. It is preferable, however, that the container-holding tray is configured to hold a plurality of bottomed cylindrical medical containers 50 in a state that the opening 52 thereof is faced downward (namely, the bottom surface part 2 side) as the container-holding tray 1 shown in FIG. 7 or the container-holding tray 101 shown in FIG. 11. According to the above-mentioned holding form, even if droplets of water are adhered to the outer surface of the medical containers 50 during the high-pressure steam sterilization, the droplets of water flow down along the outer surface of the medical containers 50 to the bottom surface part 2, 102 of the tray. Accordingly, the droplets of water do not directly flow into the inside of the medical containers 50 from the opening part 52 of the medical containers 50.

The container-holding tray according to the present invention includes the bottom surface part 2, 102 and the container holding convex part 4, 104 as the essential constituent components and the side wall part 8, 108 if needed, as the container-holding tray 1 shown in FIG. 1 or the container-holding tray 101 shown in FIG. 11. Hereinafter, the respective constituent components will be explained separately.

[2-1] Container Holding Convex Part:

The container-holding tray according to the present invention includes the container holding convex part 4, 104 configured to hold the medical containers as the container-holding tray 1 shown in FIG. 1 or the container-holding tray 101 shown in FIG. 11. A plurality of the container holding convex parts 4, 104 are formed in the bottom surface part 2, 102.

In the container-holding tray according to the present invention, each of the container holding convex parts 4, 104 is formed to have a tapered shape that is thick on the lower end side thereof and is thin on the upper end side thereof, as the container-holding tray 1 shown in FIG. 1 or the container-holding tray 101 shown in FIG. 9. By forming in the above-mentioned shape, as shown in FIG. 5 and FIG. 6, a mutual interval among three or four of the container holding convex parts 4 constituting the container housing part 6 becomes broader on the opening part side (upper end side) of the tray and becomes narrower on the bottom surface part side (lower end side) of the tray. In other words, the inner space of the container housing part 6 (container holding space) becomes a space that has an opening area being broader on the opening part side (upper end side) of the tray and being narrower on the bottom surface part side (lower end side) of the tray. Accordingly, when the medical containers 50 are housed in the container housing part as shown in FIG. 7 or FIG. 11, the medical containers 50 are brought into contact and held at intermediate points thereof in the height direction of the container housing part, thus the opening ends 54 of the medical containers 50 are kept in a state of non-contact with the bottom surface part 2, 102 of the tray.

As long as the container holding convex part has the tapered shape, the specific shape thereof is not particularly limited. For example, a truncated cone shape; a truncated pyramid shape such as a truncated quadrangular pyramid shape; a different diameter cylindrical shape; other shapes (approximately truncated pyramid shape and the like) equivalent to these shapes and the like are included. The container-holding tray 1 shown in FIG. 1 to FIG. 7 is an example configured such that the container holding convex part 4 has an approximately truncated quadrangular pyramid shape. More specifically, as shown in FIG. 4 to FIG. 6, the container holding convex part 4 has a truncated square pyramid shape as a basic shape configured such that the bottom surface is a square, and the corners of the four sides directed for the bottom surface of the truncated square pyramid are rounded (subjected to C-chamfering). On the other hand, the container-holding tray 101 shown in FIG. 9 to FIG. 11 is an example configured such that the container holding convex part 104 has an approximately different diameter cylindrical shape. More specifically, the container holding convex part 104 has a different diameter cylindrical shape in which the bottom surface side has a cylindrical shape of a larger diameter and the top surface side has a cylindrical shape of a smaller diameter as a basic shape, and has a shape in which the edge parts of the top surface are rounded (subjected to R-chamfering).

Further, the "tapered shape" does not mean only the shape that is gradually thinned from the lower end side toward the upper end side of the container holding convex part as a truncated cone shape and truncated pyramid shape. Namely, the "tapered shape" includes all the shapes that have a large diameter part having a thick outer diameter on the lower end side and a small diameter part having a thin outer diameter on the upper end side. For example, as the container holding convex part 4 shown in FIG. 6, it is preferable that the container holding convex part includes the large diameter part 10 located on the lower end side, the small diameter part 12 located on the upper end side, and the step part 14 connecting the large diameter part 10 and the small diameter part 12, and having a diameter narrowed from the large diameter part 10 toward the small diameter part 12. As mentioned above, it is preferable that the step part 14 is formed in the container holding convex part 4, since the shoulder part of the medical container 50 can be brought into contact with and held by the step part 14 as shown in FIG. 7, and the medical containers 50 can be stably held. Also, the container holding convex part 104 of the container-holding tray 101 shown in FIG. 11 is formed in a shape that has the large diameter part, the small diameter part and the step part. Accordingly, the shoulder part of the medical container 50 can be brought into contact with and held by the step part and the medical containers 50 can be stably held.

In the container-holding tray according to the present invention, a plurality of the container holding convex parts are configured to be a lattice arrangement or a zigzag arrangement on the bottom surface part. The container holding convex parts are arranged in a regular pattern such as the lattice arrangement or the zigzag arrangement, thereby the container housing part surrounded by a plurality of the container holding convex parts can be also formed regularly in parallel.

The "lattice arrangement" means an arrangement configured such that basic patterns are repeated longitudinally and horizontally, the basic patterns being configured such that the container holding convex part is located in vertexes of a square or a rectangle. In the "lattice arrangement", a plurality of the container holding convex parts are arranged so as to form lines and columns longitudinally and horizontally. On the other hand, the "zigzag arrangement" means an arrangement configured such that basic patterns are repeated alternately, the basic patterns being configured such that the container holding convex part is located in vertexes of an equilateral triangle or an isosceles triangle. It can be said that the zigzag arrangement is an arrangement configured such that the container holding convex parts are dislocated from each other by a half pitch on the basis of the lattice arrangement, the container holding convex parts belonging to the lines or columns neighboring to each other.

The container-holding tray 1 shown in FIG. 3 and the container-holding tray 101 shown in FIG. 10 are an example configured such that the container holding convex parts 4, 104 are arranged to be the lattice arrangement. More specifically, an arrangement in which basic patterns are repeated longitudinally and horizontally (a square arrangement) is employed, the basic patterns being configured such that the container holding convex parts 4, 104 are located in vertexes of a square. The container-holding tray 1 shown in FIG. 3 and the container-holding tray 101 shown in FIG. 10 are formed so as to have an approximately rectangular shape in planar view from above, and the lines and columns of the container holding convex parts 4, 104 are arranged along the long sides and short sides of the container-holding tray 1. However, as long as basic patterns configured such that the container holding parts are located in vertexes of a square or a rectangle are repeated, an arrangement in which the lines and columns of the container holding convex parts are not located along the sides of the tray (for example, an arrangement in which the lines and columns are located in an oblique direction to the sides of the tray, and so on) is included in the "lattice arrangement" described in the present invention.

In the container-holding tray according to the present invention, the container holding convex parts are configured such that three or four thereof neighboring to each other are integrated so as to surround an inner space thereof, thereby the container housing part corresponding to one medical container is formed. According to the above-mentioned configuration, each of the medical containers can be held in such a manner that it is surrounded from the outer periphery side, thus it becomes possible to stably hold the medical containers by a simple method.

For example, the container-holding tray 1 shown in FIG. 4 and the container-holding tray 101 shown in FIG. 10 are configured such that the container holding convex parts 4, 104 are arranged so as to be the lattice arrangement, four of the container holding convex parts 4, 104 neighboring to each other are integrated so as to surround an inner space thereof, thereby the container housing part corresponding to one medical container is formed.

In case that the container holding convex parts are arranged so as to be the zigzag arrangement (not shown), three of the container holding convex parts neighboring to each other are integrated so as to surround an inner space thereof, thereby the container housing part corresponding to one medical container is formed.

The container-holding tray is configured such that the medical container is brought into contact with the three or four of the container holding convex parts constituting the container housing part at any point from the upper end to the lower end of the convex parts so as to be held.

In the above-mentioned configuration, the medical containers are brought into contact with and held by the container holding convex parts at intermediate points in the height direction of the container holding convex parts. Incase that the container holding convex parts are arranged so as to be the lattice arrangement, the medical containers are brought into contact with and held by four points, and in case that the container holding convex parts are arranged so as to be the zigzag arrangement, the medical containers are brought into contact with and held by three points.

It is preferable that the container housing part is configured such that the upper end side thereof (the upper end side of the container holding convex part) is formed larger than the barrel part of the medical container and simultaneously the lower end side thereof (the lower end side of the container holding convex part) is formed smaller than the barrel part of the medical container, for the purpose of allowing the medical containers to be brought into contact therewith and held thereby. In the above-mentioned configuration, the barrel parts of the medical containers are brought into contact with and held by the container holding convex parts constituting the container housing part.

For example, in the container housing part 6 of the container-holding tray 1 shown in FIG. 6, the small diameter part 12 of the container holding convex part 4 is located on the upper end side of the container housing part 6, thus mutual intervals between the container holding convex parts 4 is configured to be broader. In addition, the upper end side of the container housing part 6 is formed to be larger than the barrel part of the medical container. On the other hand, on the lower end side of the container housing part 6, the large diameter part 10 of the container holding convex part 4 is located, thus mutual intervals between the container holding convex parts 4 is configured to be narrower. In addition, the lower end side of the container housing part 6 is formed to be smaller than the barrel part of the medical container. In the above-mentioned configuration, as shown in FIG. 7, the barrel parts of the medical containers 50 are brought into contact with and held by the step parts of the container holding convex parts 4. Also, the container-holding tray 101 shown in FIG. 11 includes the container housing part that has the same structure as the container housing part of the container-holding tray 1 shown in FIG. 6. Consequently, as shown in FIG. 11, the barrel parts of the medical containers 50 are brought into contact with and held by the step parts of the container holding convex parts 104.

It is preferable that the container-holding tray according to the present invention is configured such that the end of the opening of the medical containers is kept in a state of non-contact with the bottom surface part of the tray. By the above-mentioned configuration, even if the medical containers are held in a state that the opening is faced downward, the insides of the medical containers can be surely sterilized at the time of the high-pressure steam sterilization.

In order to keep the end of the opening of the medical containers in a state of non-contact with the bottom surface part of the tray, the length from the points at which the medical containers are brought into contact with and held by the container holding convex parts to the lower end (namely the bottom surface part of the tray) is only required to be formed longer than the total length of the shoulder part and the neck part of the medical container. More specifically, as the container-holding tray 1 shown in FIG. 7 or the container-holding tray 101 shown in FIG. 11, it is preferable that the container holding convex parts 4, 104 are formed such that the length from the step part to the lower end of the container housing part (namely the bottom surface parts 2, 102 of the tray) becomes longer than the total length of the shoulder part and the neck part of the medical container 50.

[2-2] Bottom Surface Part:

The container-holding tray according to the present invention includes the bottom surface parts 2, 102 as the container-holding tray 1 shown in FIG. 1 or the container-holding tray 101 shown in FIG. 9. The area and the like of the bottom surface part may be appropriately determined dependent on the number of the container to be held.

It is preferable that a plurality of the ventilation grooves are formed in the bottom surface part so as to pass through between the plurality of container holding convex parts. The container-holding tray according to the present invention is configured such that the end of the opening of the medical containers and the bottom surface part of the tray are kept in a state of non-contact with each other, and gaps are formed between the end of the opening of the medical containers and the bottom surface part of the tray, thus the grooves do not necessarily need to be formed for the purpose of ventilation. By forming the grooves, however, the high pressure steam flows along the above-mentioned grooves at the time of the introduction thereof, thus the high pressure steam can be easily introduced into the inside of the container. Consequently, the high-pressure steam sterilization can be carried out surely to the inside of the container.

In case that a plurality of the container holding convex parts are arranged to be the lattice arrangement, it is preferable that a plurality of the ventilation grooves are formed so as to pass through between the columns or between the lines of the plurality of the container holding convex parts. For example, in the container-holding tray 1 shown in FIG. 3 and FIG. 4, a plurality of the container holding convex parts 4 are arranged to be the lattice arrangement, and a plurality of the ventilation grooves 16 are formed in the lattice shape that passes through between all the columns and between all the lines of the container holding convex parts 4. However, the container-holding tray according to the present invention does not necessarily need to be configured such that the ventilation grooves are formed therein. For example, the container-holding tray 101 shown in FIG. 10 is an example of the tray in which the ventilation grooves are not formed.

The cross sectional shape of the grooves is not particularly limited, but it may be formed in a desired shape. For example, it can be formed in a shape such as a U-shaped groove, a V-shaped groove. Also, the depth of the grooves is not particularly limited. For example, it is preferred to be formed so as to have a depth of 0.5 to 3 mm.

[2-3] Side Wall Part:

It is preferable that the container-holding tray according to the present invention includes the side wall parts 8, 108 that stand up so as to surround the bottom surface parts 2, 102 as the container-holding tray 1 shown in FIG. 1 or the container-holding tray 101 shown in FIG. 9. The side wall part 8, 108 shown in the drawings is configured to have a step part in the middle thereof in the height direction and to stand up so as to be inclined toward the outside of the tray. However, the side wall part can be also configured to stand upright upward from the bottom surface part.

The side wall part may be formed in a plane shape, but it is preferable that it is configured such that depressions (the pockets 18, 118) that have a complementary shape with a part of the container shape are formed therein as the side wall part 8 shown in FIG. 3 or the side wall part 108 shown in FIG. 10. By this configuration, it becomes possible to hold the containers also between the pocket 18, 118 and the container holding convex part 4, 104.

The shape of the pocket may be appropriately formed in accordance with the container shape. For example, in case that the container is a container such as a vial that has an approximately circular cylindrical shape, as shown in FIG. 3 or FIG. 10, the pocket 18, 118 may be formed to have a concave curved surface complementary with a part of the peripheral surface of an approximately circular cylindrical shape.

The forming position of the pocket is not particularly limited. The container-holding tray 1 shown in FIG. 3 is an example of a tray configured such that the corner pockets 20 are formed at the four corner parts of the tray and a large number of the side pockets 22 are formed along the four sides of the tray. On the other hand, the container-holding tray 101 shown in FIG. 10 is an example of a tray configured such that a large number of the side pockets 122 are formed along the four sides of the tray, but the corner pockets are not formed at the four corner parts of the tray.

[2-4] Others:

It is preferable that the container-holding tray is comprised of materials that have a light weight and a heat-resistance capable of withstanding the high-pressure steam sterilization. Specific materials are not particularly limited, but the tray is comprised of preferably resin materials, and more preferably a thermoplastic resin among those resins. The thermoplastic resin is appropriately used, since it has excellent moldability and the tray body part (the bottom surface part and the side wall part) and the container holding convex parts can be integrally molded. Specifically, it is preferable that the tray is comprised of a polyolefin resin such as polyethylene, polypropylene.

The thickness of the container-holding tray is not particularly limited. Although the thickness varies depending on the material and structure, it is preferable that the thickness thereof is 0.5 to 2 mm. By adopting the above-mentioned range, a container-holding tray that has a light weight and a sufficient strength capable of withstanding use can be configured.

The molding method of the container-holding tray is not particularly limited. For example, the conventionally known molding method such as a vacuum molding, an injection molding can be used. As the container-holding tray 1 shown in FIG. 1, in case that the container holding convex part 4 has a linear shape, it is preferred to mold it by the vacuum molding that is capable of faithfully reproducing the shape thereof. On the other hand, as the container-holding tray 101 shown in FIG. 9, in case that the container holding convex part 104 has a curvilinear shape, it is preferred to mold it by the injection molding that is good in productivity.

EXAMPLES

Hereinafter, the present invention will be described specifically giving Examples and Comparative Examples. However, the present invention is not limited to only the constitutions of Examples described below.

Example 1

Container-holding trays that differ from the container-holding tray 1 shown in FIG. 1 to FIG. 7 only in the number of the container holding convex part 4 were manufactured. Since a basic structure thereof is the same as that of the container-holding tray 1, hereinafter an explanation will be carried out referring to FIG. 1 to FIG. 7. The container-holding tray 1 was configured to have an approximately rectangular shape in a plan view from the upper side and to have a size as a whole that is 400 mm long, 300 mm wide and 45 mm high. The container-holding tray 1 was manufactured by using a polypropylene resin as a raw material and by the vacuum molding. The container-holding tray 1 was configured to have a thickness of 1.0 mm.

As the medical container that is an object to be held, the medical container 50 (vial) as shown in FIG. 8 was conceived. The medical container 50 is a vial configured such that the volume is approximately 5 ml, the whole height is 38 mm, the outer diameter of the barrel part 56 is 22 mm, the height of the barrel part 56 is 25 mm, the outer diameter of the neck part 58 is 17 mm and the outer diameter of the opening part 52 (lip) is 20 mm.

On the bottom surface part 2 of the tray, 140 pieces of the container holding convex parts 4 were arranged. Each of the container holding convex parts 4 was configured to have an approximately truncated quadrangular pyramid shape. More specifically, as shown in FIG. 4 to FIG. 6, the container holding convex parts 4 has a truncated square pyramid shape as a basic shape configured such that the bottom surface is a square of which one side is 15 mm, the top surface is a square of which one side is 8 mm, the height is 20 mm, and the corners of the four sides directed for the bottom surface of the truncated square pyramid shape are rounded (subjected to C-chamfering). The height to the step part 14 of the container holding convex part 4 was configured to be 14 mm. The arrangement pattern of the container holding convex parts 4 was configured to be a square arrangement of 14 lines, 10 columns and 24 mm pitch. In this structure, as shown in FIG. 7, gaps of approximately 2 mm were formed between the end of the opening 54 of the containers and the bottom surface part 2 of the tray when the medical containers 50 were held by the container housing part.

In the bottom surface part 2 of the tray, the ventilation grooves 16 were formed in the lattice shape that passes through between all the 10 columns and between all the 14 lines of the container holding convex parts 4 arranged in the square arrangement. The groove was configured to be a U-shaped groove and the depth thereof was configured to be 1.0 mm.

In the side wall part 8, the pockets 18 configured to have a concave curved surface complementary with a part of the peripheral surface of the medical containers 50 were formed.

The corner pockets 20 were formed in the four corner parts of the tray and the side pockets 22 were formed in 13×2 places along the long side and in 9×2 places along the short side of the tray.

Example 2

The container-holding tray 101 shown in FIG. 9 to FIG. 11 was manufactured. The container-holding tray 101 was configured to have the same shape in a plan view from the upper side, the size as a whole, the raw material, the thickness, and the object to be held as the container-holding tray of Example 1. However, it was manufactured by the injection molding.

On the bottom surface part 102 of the tray, 140 pieces of the container holding convex parts 104 were arranged. Each of the container holding convex parts 104 has an approximately different diameter cylindrical shape. More specifically, the different diameter cylindrical shape has a basic shape that is constituted of one cylindrical shape on the bottom surface side and another cylindrical shape on the top surface side, the one cylindrical shape being configured such that the outer diameter is 13.7 mm Ø and the height is 14.5 mm, and the another cylindrical shape being configured such that the outer diameter is 12.0 mm Ø and the height is 5.5 mm, and the basic shape being configured such that the edge parts of the top surface thereof are rounded (subjected to R-chamfering (R: 3.0 mm)). Namely, the height to the step part of the container holding convex part 104 was configured to be 14.5 mm. The arrangement pattern of the container holding convex parts 104 was configured to be a square arrangement of 14 lines, 10 columns and 24 mm pitch. In this structure, as shown in FIG. 11, gaps of approximately 2 mm were formed between the end of the opening 54 of the containers and the bottom surface part 102 of the tray when the medical containers 50 were held by the container housing part.

Further, the container-holding tray 101 was configured such that the ventilation grooves were not formed in the bottom surface part 102.

In the side wall part 108, the pockets 18 configured to have a concave curved surface complementary with a part of the peripheral surface of the medical containers 50 were formed. The side pockets 122 were formed in 15×2 places along the long side and in 11×2 places along the short side of the tray. Further, the corner pocket was not formed in the container-holding tray 101.

REFERENCE SIGNS LIST 1, 101: container-holding tray, 2, 102: bottom surface part, 4, 104: container holding convex part, 6: container housing part, 8, 108: side wall part, 10: large diameter part, 12: small diameter part, 14: step part, 16: ventilation groove, 18, 118: pocket, 20: corner pocket, 22, 122: side pocket, 50: medical container, 52: opening part, 54: opening end, 56: barrel part, 58: neck part, 60: shoulder part.

The invention claimed is:
1. A container-holding tray holding a plurality of bottomed cylindrical medical containers side by side, comprising:
the container-holding tray; and
the plurality of bottomed cylindrical medical containers, wherein the container-holding tray comprises:
a bottom surface part; and
container holding convex parts formed on the bottom surface part and holding the medical containers,
each of the bottomed cylindrical medical containers has a bottom portion at a bottom of a cylindrical body and an opening on top thereof surrounded by an edge portion,
each of the container holding convex parts has a tapered shape that is thick on a lower end side and is thin on an upper end side,
the plurality of the container holding convex parts are in a lattice arrangement on the bottom surface part, and simultaneously an inner space surrounded by four of the container holding convex parts neighboring to each other forms a container housing part that holds the bottomed cylindrical medical container, the container housing part contacts and holds one of the plurality of bottomed cylindrical medical containers at contacting points located between the upper end side and the lower end side of the four of the container holding convex parts forming the container housing part and between a top and a bottom of the container, and the container-holding tray having a plurality of container housing parts holds the plurality of bottomed cylindrical medical containers side by side with the opening of each of the bottomed cylindrical medical containers facing downward and prevents, with the container holding convex parts having the tapered shape, the edge portion surrounding the opening from contacting the bottom surface part of the container-holding tray.

2. The container-holding tray holding a plurality of bottomed cylindrical medical containers side by side according to claim 1, wherein an upper end side of the container housing parts is larger than a barrel part of the bottomed cylindrical medical containers, and the lower end side of the container housing part is smaller than the barrel part of the bottomed cylindrical medical container, the barrel part of the bottomed cylindrical medical container contacts the container holding convex parts that form the container housing part at the contacting points between the upper end side and the lower end side of the respective container holding convex parts.

3. The container-holding tray holding a plurality of bottomed cylindrical medical containers side by side according to claim 1, wherein the tapered shape of the container holding convex parts is a shape gradually thinned from the lower end side toward the upper end side thereof so as to be in a truncated cone shape or a truncated pyramid shape.

4. The container-holding tray holding a plurality of bottomed cylindrical medical containers side by side according to claim 1, wherein the bottomed cylindrical medical container comprises: a barrel part at a bottom side of the container; a neck part located at an upper side of the container and having a smaller diameter than a diameter of the barrel part; a shoulder part connecting the barrel part and the neck part of the container, the bottomed cylindrical medical container contacts the container holding convex parts at the shoulder part of the container, and a length of the container holding convex parts from the contacting point, at which the container holding convex parts contact the shoulder of the bottomed cylindrical medical container, to a bottom end of the respective container holding convex parts is longer than a total length of the shoulder part and the neck part of the container.

5. The container-holding tray holding a plurality of bottomed cylindrical medical containers side by side according to claim 1, wherein the bottomed cylindrical medical container comprises: a barrel part at a bottom side of the container; a neck part located at an upper side of the container and having a smaller diameter than a diameter of the barrel part; a shoulder part connecting the barrel part and the neck part of the container, the container holding convex part comprises a large diameter part at the lower end side, a small diameter part having a smaller diameter than a diameter of the large diameter part at the upper end side, and a step part connecting the large diameter part and the small diameter part, the container holding convex part and the bottomed cylindrical medical container contact at the step part of the container holding convex part and the shoulder of the container as the contacting points between the bottomed cylindrical medical container and the container holding convex part, and a length of the container holding convex parts from the step part thereof to a bottom end of the respective container holding convex parts is longer than a total length of the shoulder part and the neck part of the bottomed cylindrical medical container.

* * * * *